United States Patent [19]

Matsumoto et al.

[11] Patent Number: 5,763,028
[45] Date of Patent: Jun. 9, 1998

[54] DOUBLY-PACKAGED EASILY OXIDIZABLE ARTICLE

[75] Inventors: Shinichi Matsumoto; Norishige Matsuo; Sachiyo Ito, all of Kawasaki, Japan

[73] Assignee: Ajinomoto Co., Inc., Tokyo, Japan

[21] Appl. No.: 607,197

[22] Filed: Feb. 26, 1996

Related U.S. Application Data

[63] Continuation of Ser. No. 257,192, Jun. 8, 1994, abandoned.

[30] Foreign Application Priority Data

Jun. 8, 1993 [JP] Japan ................................. 5-163246
May 24, 1994 [JP] Japan ................................. 6-109902

[51] Int. Cl.$^6$ ................. B65B 11/58; A23L 3/005
[52] U.S. Cl. ................. 428/34.7; 428/35.2; 428/35.4; 428/336; 428/113; 428/124; 428/127; 428/412; 206/484.2; 53/425; 53/427; 53/449
[58] Field of Search ................. 426/412, 124, 426/126, 127, 113, 107, 234; 428/34.6, 35.7, 35.2, 35.3, 349, 34.7, 35.4, 336; 53/425, 427, 440, 449; 206/484, 484.2; 604/403

[56] References Cited

U.S. PATENT DOCUMENTS

| | | | |
|---|---|---|---|
| 4,548,852 | 10/1985 | Mitchell | 426/412 |
| 4,798,728 | 1/1989 | Sugisawa | 426/124 |
| 4,928,474 | 5/1990 | Schirmer | 53/425 |
| 4,961,944 | 10/1990 | Matoba et al. | 426/127 |
| 4,986,995 | 1/1991 | Kobayashi et al. | 426/412 |
| 5,100,720 | 3/1992 | Sawada et al. | 428/215 |

FOREIGN PATENT DOCUMENTS

| | | |
|---|---|---|
| 0 067 420 | 12/1982 | European Pat. Off. |
| 0 240 571 | 10/1987 | European Pat. Off. |
| 0368601 | 5/1990 | European Pat. Off. |
| 41 02 367 | 8/1992 | Germany. |
| 0227253 | 12/1984 | Japan. |
| 1378140 | 12/1974 | United Kingdom. |

*Primary Examiner*—Rena Dye
*Attorney, Agent, or Firm*—Oblon, Spivak, McClelland, Maier, & Neustadt, P.C.

[57] ABSTRACT

A doubly-packaged easily oxidizable article and a process for packaging the article are provided, wherein the deterioration of the easily oxidizable article during heat sterilization or storage is prevented. A hermetically sealed plastic vessel filled with an easily oxidizable article is double-packaged in a flexible packaging bag. The bag is made of a plastic layer having heat-sealing characteristics, an inorganic oxide layer and a plastic layer laminated in order from the inside to the outside.

24 Claims, 1 Drawing Sheet

DOUBLY-PACKAGED EASILY OXIDIZABLE ARTICLE

This application is a continuation of application Ser. No. 08/257,192, filed on Jun. 8, 1994, now abandoned.

BACKGROUND OF THE INVENTION

1. Field of the Invention

The present invention relates to a doubly-packaged easily oxidizable article comprising a hermetically sealed plastic vessel filled with an easily oxidizable article which requires heating and/or sterilization such as an easily oxidizable medical or pharmaceutical product, medical equipment, a cosmetic product, food or drugs, which is packaged with a packaging material having high oxygen barrier properties as well as resistance to heat sterilization. The invention also relates to a packaging process for preparing a doubly-packaged easily oxidizable article.

2. Description of the Related Art

Recently, many easily oxidizable articles which require heating and/or sterilizing treatment have been packed in plastic vessels, and made available after being subjected to heat sterilization treatment. However, due to insufficient oxygen barrier properties of the vessel, the easily oxidizable article is degenerated or degraded by oxygen permeating into the vessel during the heat sterilization treatment or subsequent storage.

For example, a material such as an amino acid transfusion solution containing tryptophan undergoes browning or the generation of a foreign odor and the like by oxidation. Accordingly, when a vessel filled with a medical or pharmaceutical liquid drug which is susceptible to oxidation is required to be sterilized by heating a method as described in Japanese Patent Laid Open Hei 57-206447 is employed wherein a retort is pressurized with an inactive gas to carry out high pressure sterilization in a saturated steam atmosphere which is essentially free from oxygen so that the sample content is neither oxidized nor degenerated during heat sterilization. This method of heat sterilization however, is disadvantageous because it requires a special apparatus, a complicated procedure and high cost.

After carrying out sterilization by heat, in order to prevent the oxidation and deterioration of the desired content during storage the vessel filled with the easily oxidizable medical or pharmaceutical liquid drug is typically covered and hermetically sealed in a bag made of a laminated film having an intermediate layer that has high oxygen barrier properties, such as polyvinyl alcohol, ethylene-vinyl alcohol copolymer, polyvinylidene chloride, aluminum foil or an aluminum deposited layer and the like (Japanese Patent Laid-Open Sho 59-80256, Japanese Patent Laid-Open Hei 02-180129).

In addition in Japanese Patent Publication No. Hei 03-1021, a vessel filled with an easily oxidizable liquid drug is packaged in a sheathing bag made of a laminate having polyvinylidene chloride as an oxygen barrier layer, and sterilized by heating under that condition.

Polyvinyl alcohol and ethylene-vinyl alcohol copolymers lower their oxygen barrier properties significantly under high humidity conditions, however, and polyvinylidene chloride lowers its oxygen barrier properties significantly under high temperature conditions. When a vessel is previously packaged in a flexible packaging bag containing these materials and then heat sterilization is carried out in a retort without replacing the atmosphere with an inactive gas, it is very difficult to control the oxidation deterioration of the content during heat sterilization. In addition, the material using the polyvinyl alcohol or ethylene-vinyl alcohol copolymer attains an extremely low oxygen barrier property after heat sterilization treatment; thus the oxidation deterioration controlling capability available to protect the liquid drug during storage is very much lowered as well.

Since a product using polyvinylidene chloride also lowers the oxygen barrier properties with heat sterilization treatment considerably as shown in Japanese Patent Publication No. Hei 03-1021, though not so much as that of polyvinyl alcohol or ethylene-vinyl alcohol copolymer, it is not favorable to carry out heat sterilization treatment of the vessel while it is packaged in such a sheathing bag and to store it in such a bag, at least from the viewpoint of preventing the easily oxidizable article from being oxidized and deteriorated.

On the other hand, when a metal foil such as aluminum foil, or a film where a metal such as aluminum is deposited is used for the flexible packaging bag to carry out the sterilization by heat, the inside of the vessel cannot be seen, and visual inspection of the content for determining a foreign matter after the heat sterilization treatment is impossible. Moreover, the heat sterilization treatment tends to generate pin holes etc. which lowers the oxygen barrier properties thereof.

For the above reasons, the packing of a vessel in a flexible packaging bag having an oxygen barrier material therein is practically required to be carried out after heat sterilization treatment. Accordingly, processes for packaging a vessel in a flexible packaging bag generally comprise the steps of waiting until the vessel is cooled after heat treatment, wiping off the water on the surface, and packaging it in an inactive gas atmosphere. Such a method is disadvantageous since it is complicated, time-consuming and requires a special apparatus.

Also known in the art is a flexible plastic bag in which a film having high oxygen barrier properties, such as polyvinylidene chloride, is laminated, directly filled with a medical and pharmaceutical liquid drug, and then subjected to heat sterilization treatment (Japanese Patent Laid-Open Sho 63-164950, Japanese Patent Laid-Open Hei 02-204033). As mentioned before, however, a product utilizing polyvinylidene chloride has lowered oxygen barrier properties during and after heat sterilization. Also, when the plastic bag is contacted directly with a medical or pharmaceutical liquid drug, its ingredients migrate into the liquid drug.

There is another known process (Japanese Patent Laid-Open Sho 60-236651) wherein a silicone layer having oxygen barrier properties is formed on an external surface or an internal surface of a vessel, then the vessel is filled with a liquid drug and heat sterilization treatment is carried out under pressure after replacing the atmosphere of the autoclave with an inactive gas.

However, the oxygen permeability of such a vessel is high and is insufficient to prevent the oxidation of an easily oxidizable article. Further, the silicone layer existing on the surface of the vessel under unprotected conditions tends to be damaged, and that increases oxygen permeability. For heat sterilization, the atmosphere of the autoclave must be replaced with an inactive gas and the autoclave must be pressurized, thus the procedure is complicated and requires a special apparatus.

There is still another known process (Japanese Patent Laid-Open Sho 62-103139, Japanese Patent Laid-Open Sho 63-186652, Japanese Patent Laid-Open Hei 03-244535)

wherein a plastic bag or pouch having oxygen barrier properties in which silicon oxide layer or aluminum oxide layer is laminated, is directly filled with a medical and pharmaceutical liquid drug or food and subjected to heat sterilization treatment. In such a case, however, when the plastic bag or pouch is directly contacted with the medical and pharmaceutical liquid drug or food, the components of the plastic bag or pouch migrate into the medical and pharmaceutical liquid drug or food and lower safety, or cause a foreign taste or foreign odor. Since a material having the silicon oxide layer or aluminum oxide layer cannot be processed by blow molding, when a plastic bag for transfusion is to be produced, for example, a stick-shaped liquid drug injection nozzle must be attached later, and the attachment step tends to provide pin holes in the silicon oxide layer or aluminum oxide layer which results in lowering oxygen barrier properties.

OBJECTS OF THE PRESENT INVENTION

One object of the present invention is to provide a packaged easily oxidizable article, comprising a hermetically sealed vessel filled with the easily oxidizable article which allows for sterilization by heat under oxygen barrier conditions, prevents the components of the vessel from migrating to the easily oxidizable article, and has high inhibitory power on the oxidation deterioration of the easily oxidizable article during storage since the oxygen barrier properties are maintained at a high level even after the heat sterilization.

Another object of the present invention is to provide a process of making the packaged easily oxidizable article.

DETAILED DESCRIPTION OF THE PREFERRED EMBODIMENTS

The present invention is achieved by filling a vessel which has heat resistance, which does not, or only minimally allows its components to migrate to its contents, and which can firmly prevent components outside from permeating into it, with an easily oxidizable article and packaging the vessel in a flexible packaging bag which has high heat resistance and high oxygen barrier properties, keeps the oxygen barrier properties at a high level even under conditions of high humidity and high temperature such as during sterilization by heat, and which does not loose its high oxygen barrier properties even after, e.g., heat sterilization.

More particularly, the present invention provides a double-packaged easily oxidizable article comprising a flexible packaging bag in which one or more plastic vessels, each filled with an easily oxidizable article, are packaged and hermetically sealed. The flexible packaging bag is flexible and comprises a plastic layer having at least heat-sealing characteristics, an inorganic oxide layer and a plastic layer laminated in an ascending order from the inside of the bag, to provide a doubly-packaged easily oxidizable article. Subjecting the double-packaged easily oxidizable article to heat sterilization to provide a sterilized article is also part of the invention, as is a packaging process for making the doubly-packaged easily oxidizable article.

Easily oxidizable articles to be used in the present invention are not specifically limited. Such articles contain an oxidizable component and may be articles that require heating and/or sterilization. For example, they include medical and pharmaceutical liquid drugs such as amino acid preparations, fat emulsion preparations, vitamin preparations, nucleic acid preparations, enteral feeding nutrient preparations, tube feeding nutrient preparations, and ophthalmic solutions. A representative example includes amino acid transfusion solutions. Medical equipment includes a tube to be introduced into a body cavity or an instrument for blood transfusion which is made of a material susceptible to oxidation. Cosmetic products are also included, such as milky lotions, lotions and creams containing proteins such as collagen and chitin, amino acids, amino acid derivatives, unsaturated fatty acids and vitamins. Foods are included, for example, margarine, mayonnaise and beverages and the like which may optionally be enriched with vitamin E or unsaturated fatty acids. In addition to these, drugs and foods which require heat reaction are also included as examples.

The vessel to be filled with the easily oxidizable article is preferably a vessel made of a transparent plastic which allows visual observation of the contents. The hardness of the vessel depends on the use. Soft bags are appropriate for transfusion solutions, for example, and hard vessels are appropriate for ophthalmic solutions and the like. As the vessel material, any material can be used as long as it has such heat resistance that can resist sterilization by heat, as long as it allows little or no migration of its components into the easily oxidizable article filled in the vessel, and as long as it can prevent any component other than a gas from migrating from the outside to the easily oxidizable article through the vessel. Such a material includes, for example, a single layer or a laminated layer of a polyolefin material such as polyethylene, polypropylene, polybutene or their copolymers, as well as that of vinyl chloride, crosslinked ethylene-vinyl acetate copolymer resin, polyester, polycarbonate, polyacrylate, polyamide, and fluorine resin and the like. The vessel can be made by molding, by heat sealing, blow molding, orientation-blow molding and the like.

The flexible packaging bag is made of a laminate comprising a plastic layer having at least heat-sealing characteristics, an inorganic oxide layer and a plastic layer laminated in ascending order from the inside of the bag. The flexible packaging bag is preferably transparent to allow for visual recognition of the contents and has resistance to sterilization by heat. The oxygen permeability of the flexible packaging bag before and after typical heat sterilization treatment is not more than 4.0 ml/m$^2$ measured over 24 hours under conditions of 25° C., relative humidity of 100% and 1 atmospheric pressure (in conformance with ASTM D 3985), preferably not more than 2.0 ml/m$^2$ over 24 hours, and most preferably not more than 1.0 ml/m$^2$ over 24 hours.

BRIEF DESCRIPTION OF THE DRAWINGS

Referring to FIG. 1, reference number 1 refers to a plastic layer having heat-sealing characteristics, which comprises a single layer or two or more layers of a polyolefin such as polyethylene, polypropylene, polybutylene or their copolymers, as well as vinyl chloride, ethylene-vinyl acetate copolymer.

Figure 1:
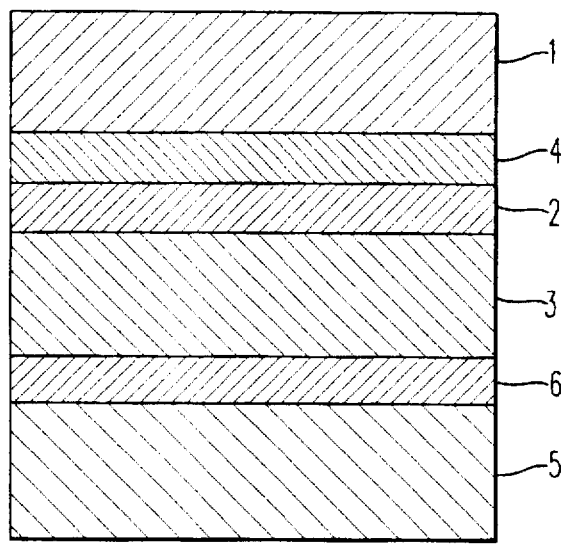
FIG. 1 is an illustrative example of a sectional view of a laminate of the present invention, but the present invention is not limited to it.

Reference number 2 refers to an inorganic oxide layer which is formed on a plastic layer 3 made of a polyester film such as biaxially oriented polyethylene terephthalate or polycarbonate, as well as a polyamide film, a polyolefin film, and a polyacrylonitrile film. As an inorganic oxide layer, any film as may be used as it has high transparency in the visible light range and high oxygen barrier properties. Examples include a silicon oxide layer, an aluminum oxide layer, a titanium oxide layer, a tin oxide layer and an indium oxide layer. Mixtures may be used. A silicon oxide layer and an aluminum oxide layer are particularly preferred. The inorganic oxide layer can be formed on both surfaces of the plastic layer 3 if desired. A plurality of plastic layers and a plurality of inorganic oxide layers can be laminated in order to improve oxygen barrier properties. In such a case, the inorganic oxide layers and plastic layers do not have to be of the same material.

For forming an inorganic oxide layer, for example, a silicon oxide layer, pre-treatment of the surface of the plastic layer 3 is not particularly needed. However, in some cases, the surface can be activated by chemical processing such as hydrolysis or a discharge treatment and the like, or the surface can be treated with a chemical agent having an active residual group such as a silane coupling agent and the like.

The silicon oxide layer can be formed by depositing or sputtering silicon or silicon oxides such as silicon monoxide or silicon dioxide in a vacuum or in an inactive gas, or by reactive deposition or reactive sputtering of silicon and/or silicon oxides excluding the use of silicon dioxide alone. When a silicon oxide layer is formed, a small amount of an inorganic oxide can be mixed with the silicon or silicon oxide. A silicon oxide layer produced from a mixture of silicon monoxide and silicon dioxide provides particularly good gas barrier properties.

From the viewpoint of gas barrier properties and flexibility, the thickness of the silicon oxide layer is preferably 50–6000 angstroms, and a particularly preferable thickness is 100–1500 angstroms. The details of its formation are described, for example, in Japanese Patent Laid-Open Hei 01-252768, Japanese Patent Laid-Open Hei 02-34328, Japanese Patent Laid-Open Hei 02-122924, Japanese Patent Laid-Open Hei 03-23333, Japanese Patent Laid-Open Hei 02-221366, Japanese Patent Laid-Open Hei 04-99263, Japanese Patent Laid-Open Hei 04-115940, Japanese Patent Laid-Open Hei 04-165064, Japanese Patent Laid-Open Hei 04-337067, Japanese Patent Laid-Open Hei 04-366142, Japanese Patent Laid-Open Hei 04-251736, and Japanese Patent Laid-Open Hei 04-341560 all incorporated herein by reference.

The formation of an aluminum oxide layer does not particularly require pre-treatment of the surface of plastic layer 3; however, in some cases the surface of the plastic layer can be activated by chemical treatment such as hydrolysis or discharging treatment and the like, or can be treated with a chemical having an active residue such as a silane coupling agent and the like.

The aluminum oxide layer can be formed by deposition or sputtering of an aluminum oxide such as AlO, $Al_2O_2$, and $Al_2O_3$ in vacuum or in an inactive gas, or by so-called reactive deposition or reactive sputtering wherein aluminum is melted and evaporated and an aluminum oxide layer is formed on a substrate while oxygen gas is introduced into a vacuum vessel.

When the aluminum oxide layer is formed, an impurity metal such as aluminum, copper, iron, tungsten, molybdenum, or silicon, or zirconium oxide, magnesium oxide, tungsten oxide, molybdenum oxide, boron nitride and silicon oxide in an amount of not more than about 10% by weight can be contained. The aluminum oxide layer can be either crystalline or non-crystalline; however, non-crystalline aluminum oxide is more preferable since it has resistance to bending.

From the viewpoint of gas barrier properties and flexibility, the thickness of the aluminum oxide layer is preferably 30–5000 angstroms, and a particularly preferable thickness is 100–2000 angstroms. 30–500 and 100–200 angstroms are also preferred. Details of the formation of the aluminum oxide layer are described in, for example, Japanese Patent Laid-Open Sho 62-101428, Japanese Patent Laid-Open Sho 62-179935, Japanese Patent Laid-Open Sho 62-220330, Japanese Patent Laid-Open Sho 63-222849, Japanese Patent Laid-Open Sho 63-223163, Japanese Patent Laid-Open Hei 03-244535, Japanese Patent Laid-Open Hei 03-23933, Japanese Patent Laid-Open Hei 03-108531, and Japanese Patent Laid-Open Hei 04-257437 all incorporated herein by reference.

Plastic layer 1 having heat-sealing characteristics and inorganic oxide layer 2 are overlapped with an optional adhesive layer 4 in FIG. 1. As the adhesive layer 4, a material which has good adhesive force with plastic layer 1 as well as with the inorganic oxide layer 2, and which does not, or only minimally, lowers the gas barrier properties, can be used. Examples of such a material include a modified polyolefin adhesive agent, a polyurethane type adhesive agent, a modified polyester type adhesive agent, an epoxy resin type adhesive agent, a photo-setting resin type adhesive agent and a silicone type adhesive agent.

A plastic layer 5 made of a material which is the same as or different from that of the plastic layer 3 can optionally be further laminated on the external surface of plastic layer 3 in order to improve breaking strength, stab strength, gas barrier properties, and resistance to heat sterilization of the flexible packaging bag as a whole. As a material for the plastic layer 5, polyolefin, polyester, polyamide, polyacrylonitrile, polycarbonate, liquid crystalline polymer, silicone, a fluorine resin and the like are desirable. Such lamination can be provided between the plastic layer 1 having heat-sealing characteristics and the inorganic oxide layer 2.

A plastic layer can be further laminated on the external surface, if necessary. The plastic layer 3 and the plastic layer 5 can be adhered with an optional adhesive layer 6. An example of such adhesive agent includes a modified polyolefin adhesive agent, a polyurethane type adhesive agent, a modified polyester type adhesive agent, an epoxy resin type adhesive agent, a photo-setting resin type adhesive agent and a silicone type adhesive agent.

Another material having oxygen barrier properties such as a polyvinyl alcohol layer, an ethylene-vinyl alcohol copolymer layer or a polyvinylidene chloride layer can be laminated between plastic layer 1 and the inorganic oxide layer 2, in order to further reduce the gas permeability. In such a case, since the inorganic oxide layer has steam barrier properties, the lowering of the oxygen barrier properties of the polyvinyl alcohol layer or the ethylene-vinyl alcohol copolymer layer after the heat sterilization can be avoided.

The flexible packaging bag is formed into a bag shape by, e.g., heat-sealing of the peripheries of a pair of thus produced laminated bodies.

For the packaging process of the present invention, a vessel which is to be filled with the easily oxidizable article is firstly molded, and filled with the easily oxidizable article then hermetically sealed. When the vessel to be filled with the easily oxidizable article is a transfusion solution bag, the molding of the vessel can be done by blow molding process, or orientation blow molding process, or by attaching a liquid drug injection nozzle at the same time or immediately after the heat-sealing of the peripheries.

Figure 2:
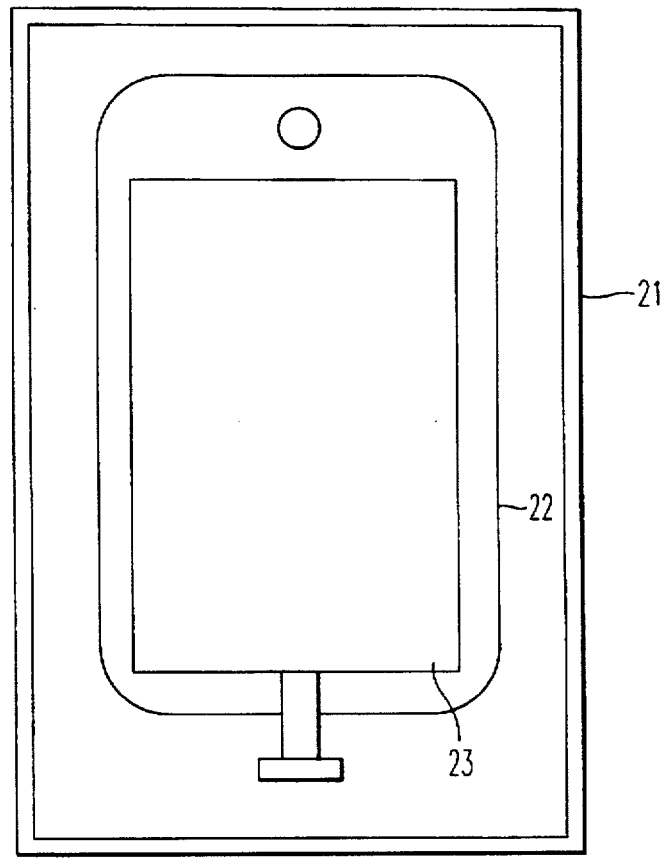
FIG. 2 is an illustrative example of the invention doubly-packaged easily oxidizable article.

One or more vessels thus filled and sealed are packaged in a flexible packaging bag formed by, e.g., a process such as sealing three sides. For packaging the vessels, a sheathing material which is already made into a bag can be used, or the vessel is held between a pair of laminated films, and the peripheries of the laminated films are heat-sealed to make a flexible packaging bag containing the vessel therein. Then either vacuum packaging, wherein the air is released from the opening of the flexible packaging bag, and the opening is heat-sealed or inactive gas flush packaging, wherein an inactive gas is blown into the bag from the opening to replace the inside atmosphere with the inactive gas, then the opening is heat-sealed, is carried out. The double-packaged easily oxidizable article thus produced is shown in FIG. 2 where 21 is the flexible bag, 22 is the vessel, and 23 is the easily oxidizable article.

Immediately after the vessel is packaged in the flexible packaging bag, heat sterilization treatment is carried out. The heat sterilization treatment is carried out by so-called retort sterilization wherein the package is kept in a high pressure steam atmosphere or hot water for a predetermined length of time. The retort sterilization is carried out in a normal retort and pressure control with an inactive gas is not required. The temperature and the time for retort sterilization are not particularly limited, but it is preferable that the easily oxidizable article be sterilized, or heat reaction completed, but not degenerated.

The sterilization treatment is normally carried out at 115° C. for 30 minutes, or at 121° C. for 20 minutes. In such a case, the pressure of the retort is made higher than the vapor pressure of the easily oxidizable article at the temperature of the sterilization by about 0.1–2.0 kg/cm$^2$, and the pressurization is controlled by blowing pressurized air. Since the flexible packaging bag has an inorganic oxide layer having high gas barrier properties, the oxygen in the pressurized air is prevented from entering, and the oxidation and deterioration of the substance in the retort can be prevented.

After all of the above steps, the visual inspection of the content is carried out. Since both the vessel to be filled with the easily oxidizable article and the flexible packaging bag are substantially transparent, the mixing of foreign matter can be easily recognized from outside. Accordingly, quality control can be easy accomplished to secure high safety. After that, the product is supplied to hospitals and the like as it is or after being packed in a box.

The above-mentioned series of packaging process steps for a doubly-packaged easily oxidizable article is preferably carried out in a continuous manner in order to prevent the degeneration or putrefaction of the contents by contacting the vessel filled with the easily oxidizable article with air.

Since the material used for the vessel filled with the easily oxidizable article does not, or only minimally allows its components to migrate to the easily oxidizable article during heat sterilization or storage and prevents outside substances except for gas from permeating, the migration of components from the flexible packaging bag into the easily oxidizable article is greatly or completely inhibited, thus providing high safety.

An oxygen adsorber, a deodorizing agent, a carbon dioxide adsorber, a drying agent, a hydrogen sulphide adsorber, a fragrance and the like can be provided between the vessel and the flexible packaging bag of the present invention, if necessary, for such purposes as avoiding the deterioration of the contents, avoiding expansion prior to the opening of the seal, and to avoid bad odor when the seal is opened.

The flexible packaging bag having an inorganic oxide layer used in the present invention has high gas barrier properties to other gasses in addition to oxygen, and it can be applied to such uses that require gas barrier properties. For example, as the bag has steam barrier properties, the entering of water from outside or diffusion of water to outside can be prevented. Accordingly, the bag can be applied to packaging a powder or a solid substance such as an amino acid or a nucleic acid which are deliquescent or which might absorb humidity and be concreted, or for packaging a substance which might be denatured by drying or a solution wherein the concentrations of the components might be changed by drying. Also it can be used for packaging a substance which is desired not to be exposed to carbon dioxide or for preventing the leaking of odor.

EXAMPLES

Some examples of the present invention follow, but the present invention is not limited to these examples. In the examples, "GT 1000R" (Trade Name) produced by Toyo Ink Mfg. Co., Ltd. was used as a silicon oxide layer/biaxially oriented polyethylene terephthalate film (thickness of 12 μm), and "VM-PET1011HG" (Trade Name) produced by Toyo Metallizing Co., Ltd. was used as an aluminum oxide layer/biaxially oriented polyethylene terephthalate film (thickness of 12 μm). For resin films having relatively high oxygen barrier properties used in reference examples, "SARAN-UB" (Trade Name) produced by Asahi Chemical Industry Co., Ltd. which was a vinylidene chloride copolymer resin (PVDC) biaxially oriented film (thickness of 15 μm), "EVAL film EF-RT" (Trade Name) produced by Kuraray Co., Ltd. which was an ethylene-vinyl alcohol copolymer resin (EVOH) film (thickness of 15 μm), and "OSM film" (Trade Name) produced by Toyobo Co., Ltd. which was a polymethaxylylene adipamide resin (MXD6) biaxially oriented film (thickness of 15 μm) were used.

The oxygen permeability of the film was measured by using "Oxtran Model 100" which is an oxygen permeability measuring apparatus produced by MODERN CONTROLS, INC., under conditions of 25° C., relative humidity of 100% and 1 atm (in conformance with ASTM D 3985).

The degree of yellowing of a tryptophan aqueous solution due to its oxidation deterioration was obtained by measuring its transmissivity (T %) at a wave length of 430 nm by using the "U-3210" which is a recording spectrophotometer produced by Hitachi Ltd.

The degree of elution of the components of a bag material into an aqueous solution packed in the bag was obtained by measuring the absorbency of the solution by the above-mentioned recording spectrophotometer at wave lengths of 210 nm, 220 nm and 240 nm.

Example 1

Two opposed non-oriented polypropylene films (thickness of 110 μm) were cut to a size of 150 mm×190 mm, three sides were sealed in a width of 5 mm, and 200 ml of a tryptophan solution having an L-tryptophan concentration of 0.4 g/dl and pH of 6.6, which was prepared from deoxygenated water, was packed through the opening immediately after the preparation of the solution. Then the atmosphere was replaced with nitrogen gas, and the opening was heat-sealed hermetically.

The packaged solution was immediately put in a flexible packaging bag which was produced by sealing 3 sides of two laminated films of 180 mm×210 mm, in a width of 5 mm, the film having a structure of non-oriented polypropylene (thickness of 70 μm)/polyurethane adhesive agent (5 g/m$^2$) /silicon oxide layer/biaxially oriented polyethylene terephthalate (thickness of 12 μm), keeping the non-oriented polypropylene side inside, then the bag was set in a vacuum packaging vessel of an automatic vacuum gas packaging machine, model "FVS-420-G" produced by Furukawa Seisakusho Co., Ltd. in such a way that the opening of the flexible packaging bag could be heat-sealed, then the pressure inside of the vacuum packaging vessel was reduced by an oil hydraulic vacuum pump, to evacuate the air between the inner bag and the flexible packaging bag, and the opening of the flexible packaging bag was heat-sealed when the degree of vacuum inside of the vessel reached approximately 2 Torr. The package thus vacuum packed was placed in a retort apparatus and heat sterilization treatment was carried out in pressurized hot water at 121° C. for 30 minutes, then the package was stored under at 44° C. and a relative humidity of 80%.

The oxygen permeability of the flexible packaging bag before and after the heat sterilization was measured and the change was examined. The yellowing degree of the contents after the heat sterilization as well as during the storing test at 44° C. and under relative humidity of 80% was measured with time.

Example 2

Example 2 was carried out in a manner analogous to that of Example 1, but by replacing the pressurized hot water with high pressure steam in order to carry out the heat sterilization treatment at 121° C. for 30 minutes.

Example 3

Example 3 was carried out in a manner analogous to that of Example 1, but by replacing vacuum packaging with nitrogen gas flush packaging, in which a nitrogen gas flush nozzle was plugged into an opening of the flexible packaging bag, and the bag was set in a vacuum packaging vessel of an automatic vacuum gas packaging machine, model "FVS-420-G" produced by Furukawa Seisakusho Co., Ltd. in such a way that the opening of the flexible packaging bag could be heat-sealed after charging the gas, then the pressure inside of the vacuum packaging vessel was reduced by an oil hydraulic vacuum pump, to evacuate the air between the inner bag and the flexible packaging bag, and nitrogen gas was blown through the nozzle into a space between the inner bag and the flexible packaging when the degree of vacuum inside of the vessel reached approximately 2 Torr, till the amount of the nitrogen gas charged becomes about 10 ml, and the opening of the flexible packaging bag was heat-sealed immediately.

Example 4

Example 4 was carried out in a manner analogous to that of Example 1, except that a laminated material wherein non-oriented polypropylene (thickness of 70 μm), polyurethane adhesive agent (5 g/m$^2$), silicon oxide layer, biaxially drawn polyethylene terephthalate (thickness of 12 μm), polyurethane adhesive agent (5 g/m$^2$) and biaxially drawn polyethylene terephthalate (thickness of 12 μm) were laminated in this order from the inside, was used for the flexible packaging bag.

Example 5

Example 4 was carried out in a manner analogous to that of Example 2, except that a laminated material wherein non-oriented polypropylene (thickness of 70 μm), polyurethane adhesive agent (5 g/m$^2$), silicon oxide layer, biaxially drawn polyethylene terephthalate (thickness of 12 μm), polyurethane adhesive agent (5 g/m$^2$) and biaxially drawn polyethylene terephthalate (thickness of 12 μm) were laminated in this order from inside was used for the flexible packaging bag.

Example 6

Example 6 was carried out in a manner analogous to that of Example 1, except that a laminated material wherein non-oriented polypropylene (thickness of 60 μm), polyurethane adhesive agent (5 g/m$^2$), aluminum oxide layer, biaxially oriented polyethylene terephthalate (thickness of 12 μm), polyurethane adhesive agent (5 g/m$^2$), aluminum oxide layer and biaxially oriented polyethylene terephthalate (thickness of 12 μm) were laminated in this order from the inside, was used for the flexible packaging bag.

Example 7

Example 7 was carried out in a manner analogous to that of Example 1, but by replacing the tryptophan solution with twice distilled water, and by carrying out heat sterilization at 121° C. for 20 minutes. After the heat sterilization, the degree of elution of the components of a bag material into the packed distilled water was measured.

Example 8

Example 8 was carried out in a manner analogous to that of Example 2, but by replacing the tryptophan solution with twice distilled water, and by carrying out heat sterilization at 121° C. for 20 minutes. After the heat sterilization, the degree of elution of the components of a bag material into the packed distilled water was measured.

Example 9

Example 9 was carried out in a manner analogous to that of Example 3, but by replacing the tryptophan solution with twice distilled water, and by carrying out heat sterilization at 121° C. for 20 minutes. After the heat sterilization, the degree of elution of the components of a bag material into the packed distilled water was measured.

Example 10

Example 10 was carried out in a manner analogous to that of Example 1, but by replacing the tryptophan solution with twice distilled water, and by carrying out heat sterilization at 121° C. for 20 minutes. After the heat sterilization, the degree of elution of the components of the bag material into the packed distilled water was measured.

Example 11

Example 11 was carried out in a manner analogous to that of Example 6, but by replacing the tryptophan solution with twice distilled water, and by carrying out heat sterilization at 121° C. for 20 minutes. After the heat sterilization, the degree of elution of the components of the bag material eluted into the packed distilled water was measured.

Reference Example 1

Two opposed non-oriented polypropylene films (thickness of 110 μm) were cut to a size of 150 mm×190 mm, three sides were sealed in a width of 5 mm, and 200 ml of a tryptophan solution having the L-tryptophan concentration of 0.4 g/dl and pH of 6.6, which was prepared from deoxygenated water, was packed through the opening immediately after the preparation of the solution. Then the atmosphere was replaced with nitrogen gas, and the opening was heat-sealed hermetically. This was placed in a retort apparatus without delay, and heat sterilization treatment was carried out in pressurized hot water at 121° C. for 30 minutes. Then it was stored at 44° C. and a relative humidity of 80%.

The oxygen permeability of the bag before and after the heat sterilization was measured and the change was examined. The yellowing degree of the contents after the heat sterilization as well as during the storing test at 44° C. and under relative humidity of 80% was measured with time.

Reference Example 2

Reference Example 2 was carried out in a manner analogous to that of Reference Example 1, but by replacing the pressurized hot water with high pressure steam in order to carry out the heat sterilization treatment at 121° C. for 30 minutes.

Reference Example 3

Reference Example 3 was carried out in a manner analogous to that of Reference Example 1, except that a laminated material wherein a laminated material wherein non-oriented polypropylene (thickness of 65 μm), polyurethane adhesive agent (5 g/m$^2$), biaxially oriented PVDC (thickness of 15 μm), polyurethane adhesive agent (5 g/m$^2$) and non-oriented polypropylene (thickness of 50 μm) were laminated in this order from the inside, was used for the flexible packaging bag.

Reference Example 4

Reference Example 4 was carried out in a manner analogous to that of Reference Example 2, except that a laminated material wherein a laminated material wherein non-oriented polypropylene (thickness of 65 μm), polyurethane adhesive agent (5 g/m$^2$), biaxially oriented PVDC (thickness of 15 μm), polyurethane adhesive agent (5 g/m$^2$) and non-oriented polypropylene (thickness of 50 μm) were laminated in this order from the inside, was used for the flexible packaging bag.

Reference Example 5

Reference Example 5 was carried out in a manner analogous to that of Reference Example 1, except that a laminated material wherein non-oriented polypropylene (thickness of 70 μm), polyurethane adhesive agent (5 g/m$^2$), EVOH (15 μm), polyurethane adhesive agent (5 g/m$^2$), biaxially oriented polyethylene terephthalate (thickness of 12 μm) were laminated in this order from the inside, was used for the flexible packaging bag.

Reference Example 6

Reference Example 6 was carried out in a manner analogous to that of Reference Example 1, except that a laminated material wherein non-oriented polypropylene (thickness of 70 μm), polyurethane adhesive agent (5 g/m$^2$), biaxially oriented MXD6 (15 μm), polyurethane adhesive agent (5 g/m$^2$), biaxially oriented polyethylene terephthalate (thickness of 12 μm) were laminated in this order from the inside, was used for the flexible packaging bag.

Reference Example 7

Reference Example 7 was carried out in a manner analogous to that of Reference Example 1, but by replacing the tryptophan solution with twice distilled water, and by carrying out heat sterilization at 121° C. for 20 minutes. After the heat sterilization, the degree of elution of the components of the bag material into the packed distilled water was measured.

Reference Example 8

Reference Example 8 was carried out in a manner analogous to that of Reference Example 2, but by replacing the tryptophan solution with twice distilled water, and by carrying out heat sterilization at 121° C. for 20 minutes. After the heat sterilization, the degree of elution of the components of the bag material into the packed distilled water was measured.

Reference Example 9

Two laminated films of 150 mm×190 mm, each having a structure of non-oriented polypropylene (thickness of 70 μm)/polyurethane adhesive agent (5 g/m$^2$)/silicon oxide layer/biaxially oriented polyethylene terephthalate (thickness of 12 μm), were opposed by keeping the non-oriented polypropylene side inside, and three sides were sealed in a width of 5 mm, and twice distilled water was packed through the opening, then the opening was heat-sealed hermetically. It was immediately placed in a retort apparatus and heat sterilization treatment was carried out in pressurized hot water at 121° C. for 20 minutes. After the heat sterilization, the degree of elution of the components of the bag material into the packed distilled water was measured.

Reference Example 10

Reference Example 10 was carried out in a manner analogous to that of Reference Example 9, but by replacing the pressurized hot water with high pressure steam in order to carry out the heat sterilization treatment at 121° C. for 20 minutes.

Reference Example 11

Two laminated films of 150 mm×190 mm, each having a structure of non-oriented polypropylene (thickness of 60 μm)/polyurethane adhesive agent (5 g/m$^2$)/aluminum oxide layer/biaxially oriented polyethylene terephthalate (thickness of 12 μm)/polyurethane adhesive agent (5 g/m$^2$)/aluminum oxide layer/biaxially oriented polyethylene terephthalate (thickness of 12 μm), were opposed by keeping the non-oriented polypropylene side inside, and three sides were sealed in a width of 5 mm, and twice distilled water was packed through the opening, then the opening was heat-sealed hermetically. It was immediately placed in a retort apparatus and heat sterilization treatment was carried out in pressurized hot water at 121° C. for 20 minutes. After the heat sterilization, the degree of elution of the components of the bag material into the packed distilled water was measured.

The changes in the oxygen permeability before and after the heat sterilization are shown in Table 1. The change in the nature of the tryptophan solution with time, before and after the heat sterilization as well as during the storing test are shown in Table 2.

The results show that the flexible packaging bag having the inorganic oxide layer has higher oxygen barrier properties than do others, causes less changes in its oxygen permeability before and after heat sterilization, and has high inhibitory power on the oxidation and the deterioration of the tryptophan solution, which is the content of the bag, during the heat sterilization as well as during the storing test.

Also, the degrees of elution of the components of the bag material into the packed liquid drug after the heat sterilization are compared and shown in Table 3.

This shows that elution of the components of the bag material into the packed liquid drug, as impurities, can be largely prevented by the use of the bag material having the inorganic oxide layer for a flexible packaging bag, and by the use of an inner bag made of a material which does not, or only minimally contains such components that are easily eluted into the liquid drug, and which has relatively high barrier properties to such a component that is contained within the flexible packaging bag and that is easily eluted into the liquid drug, rather than by directly filling the bag material having the inorganic oxide layer, with the liquid drug. Change of the oxygen permeability before and after the heat sterilization.

TABLE 1

OXYGEN PERMEABILITY * BEFORE AND AFTER THE HEAT STERILIZATION

|  | before | after |  | before | after |
|---|---|---|---|---|---|
| Example 1 | 0.5 | 0.8 | Reference Example 1 | 580 | 591 |
| Example 2 | 0.5 | 0.7 | Reference Example 2 | 586 | 556 |
| Example 3 | 0.5 | 0.8 | Reference Example 3 | 2.7 | 6.0 |
| Example 4 | 0.5 | 0.6 | Reference Example 4 | 2.7 | 34.5 |
| Example 5 | 0.5 | 0.6 | Reference Example 5 | 0.4 | 25.4 |
| Example 6 | 0.9 | 1.2 | Reference Example 6 | 4.2 | 20.3 |

*Unit: ml/m² 24 h atm 25° C. 100% RH

Oxidation deterioration of tryptophan solution before and after the heat sterilization and during the storing test.

TABLE 2

CHANGE IN TRANSMISSIVITY * OF 0.4 WT. % TRP AQUEOUS SOLUTION AT 430 nm

| Storing period | Example 1 | Example 2 | Example 3 | Example 4 | Example 5 | Example 6 |
|---|---|---|---|---|---|---|
| before retort | 99.6 | 99.6 | 99.6 | 99.6 | 99.7 | 99.7 |
| after retort | 98.6 | 97.7 | 98.2 | 98.5 | 98.0 | 98.3 |
| 44° C., 1 month | 89.7 | 80.0 | 85.4 | 80.5 | 84.0 | 78.2 |
| 44° C., 3 months | 44.6 | 44.1 | 46.8 | 43.0 | 44.9 | 40.2 |
| 44° C., 6 months | 19.3 | 16.1 | 20.5 | 20.0 | 20.2 | 15.2 |

| Storing period | Reference Example 1 | Reference Example 2 | Reference Example 3 | Reference Example 4 | Reference Example 5 | Reference Example 6 |
|---|---|---|---|---|---|---|
| before retort | 98.8 | 99.1 | 98.8 | 99.2 | 99 | 99.1 |
| after retort | 96.7 | 96.5 | 97.6 | 97.7 | 96.9 | 97.5 |
| 44° C., 1 month | 51.2 | 62.6 | 72.3 | 68.2 | 70.5 | 74.2 |
| 44° C., 3 months | 4.5 | 3.8 | 14.7 | 4.7 | 12.3 | 15 |

TABLE 2-continued

CHANGE IN TRANSMISSIVITY * OF 0.4 WT. % TRP AQUEOUS SOLUTION AT 430 nm

| 44° C., 6 months | 0.0 | 0.1 | 9.1 | 0.2 | 3.3 | 4.6 |

*Transmissivity at cell length of 10 mm, and a wavelength of 430 nm.

Absorbency of a substance eluted into the packed liquid drug after the heat sterilization.

TABLE 3

|  | Absorbency | | |
|---|---|---|---|
|  | 210 nm | 220 nm | 240 nm |
| Example 7 | 0.085 | 0.053 | 0.022 |
| Example 8 | 0.062 | 0.040 | 0.018 |
| Example 9 | 0.049 | 0.032 | 0.016 |
| Example 10 | 0.093 | 0.056 | 0.026 |
| Example 11 | 0.088 | 0.054 | 0.022 |
| Reference Example 7 | 0.006 | 0.005 | 0.003 |
| Reference Example 8 | 0.006 | 0.005 | 0.004 |
| Reference Example 9 | 0.398 | 0.217 | 0.081 |
| Reference Example 10 | 0.312 | 0.171 | 0.064 |
| Reference Example 11 | 0.349 | 0.191 | 0.071 |

The invention vessel filled with the easily oxidizable article is packaged with a flexible packaging bag having an inorganic oxide layer, which has little humidity and temperature dependency, and high oxygen barrier properties, wherein the oxygen barrier properties are constant or change only little before and after the heat sterilization processing; thus, the heat sterilization can be done while the vessel is packaged in the flexible packaging bag, and the oxidation and deterioration of the easily oxidizable article during heat sterilization can be prevented.

Since the high oxygen barrier properties can be maintained even after the heat sterilization, the flexible packaging bag has high inhibitory power on oxidation and deterioration of the easily oxidizable article during the subsequent storing period. Accordingly, it is not necessary to wrap the vessel filled with the easily oxidizable article again with a new bag having high oxygen barrier properties, after the heat sterilization.

The vessel filled with the easily oxidizable article does not allow its components to migrate into the contents, and highly prevents the permeation of components excluding a gas from outside, the migration of the bag material components into the contents, which is seen when the easily oxidizable article is directly filled with a bag having high oxygen barrier properties and subjected to the heat sterilization treatment, can be substantially prevented, to assure high safety of the contents for use. In addition, the doubly-packaged easily oxidizable article can be made to have transparency, and the mixing of a foreign substance into the content can be easily observed to allow easy quality control, and high safety of the contents is assured from this point of view as well.

The process of packaging the double-packaged easily oxidizable article of the present invention does not require any complicated process nor special apparatus, and has small number of steps, i.e. it is a simple process and particularly when a series of steps are carried out continuously, the production amount can be increased to lower the cost. The product can be supplied to hospitals as it is or after packed in a box.

As described above, the flexible packaging bag of the doubly-packaged easily oxidizable article of the present invention has high oxygen barrier properties, allows for the heat sterilization of the contents while they are packaged in the flexible packaging bag since it shows no or almost no change in the oxygen barrier properties before and after the heat sterilization treatment, and has a high inhibitory power on oxidation and deterioration of the easily oxidizable article during heat sterilization and storage. By providing a vessel filled with the easily oxidizable article in the flexible packaging bag, the migration of the components of the bag material into the contents can be completely or almost completely eliminated; thus the migration of the components of the bag material into the contents, that is seen when the easily oxidizable article is directly packed in a bag of high oxygen barrier capacity and then subjected to sterilization by heat, can be substantially prevented. In addition, the doubly-packaged easily oxidizable article can be made to have transparency, and the mixing of a foreign substance to the content can be easily seen from outside.

The process for packaging the doubly-packaged easily oxidizable article of the present invention does not need any complicated procedure nor any special apparatus, and requires few process steps.

This application claims priority to Japan 100902/1994, filed May 24, 1994 and Japan 163246/1993, filed Jun. 8, 1993, both incorporated herein by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A doubly-packaged oxidizable article, comprising a flexible bag in which one or more hermetically sealed plastic vessels filled with an oxidizable article are contained;
   said flexible packaging bag, comprising a laminate, comprising in ascending order:
   a) an inner plastic base layer having a heat-sealing property;
   b) a resin layer on said base layer a) having an oxygen-barrier property, which resin layer is a layer of polyvinyl alcohol, ethylene-vinyl alcohol copolymer, polyvinylidene chloride, biaxially-oriented polyethylene terephthalate, polyamide or polyester;
   c) an inorganic layer having a steam barrier property on said resin layer (b); and
   d) an outer plastic layer on said layer c);
   wherein said flexible packaging bag has an oxygen permeability before and after heat sterilization of not more than 4.0 ml/m² measured over 24 hours under conditions of 25° C., relative humidity of 100% at a pressure of 1 atm.

2. The doubly-packaged oxidizable article according to claim 1, wherein said resin layer b) on said base layer a) is a layer of polyvinyl alcohol, ethylene-vinyl alcohol copolymer, polyvinylidene chloride, biaxially-oriented polyethylene terephthalate or polyamide.

3. The doubly-packaged oxidizable article according to claim 1, wherein the inorganic oxide layer is selected from the group consisting of a silicon oxide layer, an aluminum oxide layer, a titanium oxide layer and an indium oxide layer.

4. The doubly-packaged oxidizable article according to claim 1, wherein said article has undergone sterilization by heat.

5. The doubly-packaged oxidizable article according to claim 3, wherein said article has undergone sterilization by heat.

6. The doubly-packaged oxidizable article according to claim 1, wherein the flexible bag is hermetically sealed.

7. The doubly-packaged oxidizable article according to claim 1, wherein said vessels filled with said easily oxidizable article are transparent.

8. The doubly-packaged oxidizable article according to claim 1, wherein said vessels are made of a single layer or laminated layers of a polyolefin material.

9. The doubly-packaged oxidizable article according to claim 8, wherein said polyolefin material is selected from the group consisting of polyethylene, polypropylene, polybutene and copolymers of each, polyvinyl chloride, crosslinked ethylene-vinyl acetate copolymers resin, polyester, polycarbonate, polyacrylate and polyamide.

10. The doubly-packaged oxidizable article according to claim 3, wherein said inorganic oxide layer is a silicon oxide layer or an aluminum oxide layer.

11. The doubly-packaged oxidizable article according to claim 10, wherein said inorganic oxide layer is a silicon oxide layer comprising a mixture of silicon monoxide and silicon dioxide.

12. The doubly-packaged oxidizable article according to claim 11, wherein said silicon oxide layer is from 50 to 6,000 Å in thickness.

13. The doubly-packaged oxidizable article according to claim 12, wherein said silicon oxide layer is from 100 to 1,500 Å in thickness.

14. The doubly-packaged oxidizable article according to claim 10, wherein said inorganic oxide layer is non-crystalline aluminum oxide.

15. The doubly-packaged oxidizable article according to claim 14, wherein said non-crystallilne aluminum oxide layer is 30 to 5,000 Å in thickness.

16. The doubly-packaged oxidizable article according to claim 1, wherein said resin layer b) having an oxygen-barrier property is a polyvinyl alcohol layer, an ethylene-vinyl alcohol copolymer layer or a polyvinylidene chloride layer.

17. The doubly-packaged oxidizable article according to claim 1, wherein said oxidizable article comprises amino acid preparations, fat emulsion preparations, vitamin preparations, nucleic acid preparations, entered feeding nutrient preparations, tube feeding nutrient preparations, ophthalmic solutions and foods.

18. The doubly-packaged oxidizable article according to claim 17, wherein said foods comprise margarine, mayonnaise or beverages.

19. The doubly-packaged oxidizable article according to claim 1, wherein said oxygen permeability of said flexible packaging bag before and after heat treatment is 2.0 ml/m² over 24 hours.

20. The doubly-packaged oxidizable article according to claim 19, wherein said oxygen permeability of said flexible packaging bag before and after heat treatment is 1.0 ml/m² over 24 hours.

21. A process for preparing a sterilized doubly-packaged easily oxidizable article, comprising a flexible bag in which one or more hermetically sealed plastic vessels filled with an oxidizable article are contained and hermetically sealed, which process comprises:
   a) charging the easily oxidizable article into the plastic vessel; and b) hermetically sealing the vessel and packaging the vessel in a flexible packaging bag;

said flexible packaging bag, comprising a laminate, comprising in ascending order:
  i) an inner plastic base layer having a heat-sealing property;
  ii) a resin layer on said base layer i) having an oxygen-barrier property, which resin layer is a layer of polyvinyl alcohol, ethylene-vinyl alcohol copolymer, polyvinylidene chloride, biaxially-oriented polyethylene terephthalate, polyamide or polyester;
  iii) an inorganic layer having a steam barrier property area on said resin ii); and
  iv) a plastic layer on said layer iii);

wherein said flexible packaging bag has an oxygen permeability before and after heat sterilization of not more than 4.0 ml/m² measured over 24 hours under conditions of 25° C., relative humidity of 100% and a pressure of 1 atmosphere.

22. The process according to claim 21, wherein said resin layer b) on said base layer a) is a layer of polyvinyl alcohol, ethylene-vinyl alcohol copolymer, polyvinylidene chloride, biaxcally-oriented polyethylene terephthalate or polyamide.

23. The process according to claim 21, wherein the oxgyen permeability of said flexible packaging bag before and after heat treatment is 2.0 ml/m² over 24 hours.

24. The process according to claim 23, wherein the oxgyen permeability of said flexible packaging bag before and after heat treatment is 1.0 ml/m² over 24 hours.

* * * * *